United States Patent [19]
Campbell

[11] Patent Number: 5,134,992
[45] Date of Patent: Aug. 4, 1992

[54] ADJUSTABLE SPLINT FOR THE LEG OF AN ANIMAL

[76] Inventor: Blair H. Campbell, Box 7029, Rutland, Vt. 05701

[21] Appl. No.: 673,273

[22] Filed: Mar. 21, 1991

[51] Int. Cl.$^5$ .............................................. A61F 5/04
[52] U.S. Cl. ............................................. 602/6; 602/23
[58] Field of Search .............. 128/82, 85, 87 R, 89 R, 128/90; 119/96

[56] References Cited

U.S. PATENT DOCUMENTS

| | | | |
|---|---|---|---|
| 188,804 | 9/1891 | Ellis | 128/89 R |
| 676,243 | 6/1901 | Rommel et al. | 119/127 |
| 684,411 | 10/1901 | Cook | 128/89 R |
| 1,624,861 | 4/1927 | Dewey | 119/127 |
| 2,474,634 | 6/1949 | Mason | 128/87 R |
| 3,314,419 | 4/1967 | Quick | 128/90 |
| 3,416,519 | 12/1968 | Dowers | 128/87 R |
| 3,470,873 | 10/1969 | Walker et al. | 128/89 R |
| 3,791,383 | 2/1974 | Friedman | 119/96 X |
| 3,819,966 | 6/1974 | Webster et al. | 128/90 X |
| 3,881,472 | 5/1975 | Lee | 128/89 R |
| 4,029,090 | 6/1977 | Dawson, Jr. | 128/87 R |
| 4,143,653 | 3/1979 | Wichman | 128/89 R X |
| 4,320,722 | 3/1982 | Glassman et al. | 128/85 X |
| 4,349,016 | 9/1982 | Glassman et al. | 128/87 R |
| 4,361,143 | 11/1982 | Nelson | 128/87 R |
| 4,911,150 | 3/1990 | Farley | 119/96 X |
| 4,951,656 | 8/1990 | Gorka et al. | 128/90 |

FOREIGN PATENT DOCUMENTS

| | | | |
|---|---|---|---|
| 380457 | 8/1990 | European Pat. Off. | 128/90 |
| 2599 | of 1891 | United Kingdom | 128/89 R |

OTHER PUBLICATIONS

Textbook of Small Animal Surgery vol. II, published by W. B. Saunders Company, 1985.
Literature by North Cast Medical, Inc., Hand Therapy Catalog, 1990.

*Primary Examiner*—Robert A. Hafer
*Assistant Examiner*—Kevin G. Rooney
*Attorney, Agent, or Firm*—Michael J. Weins

[57] ABSTRACT

The present invention is directed to a splint suitable for immobilizing a leg of an animal such as a dog or a cat. The splint of the present invention can be easily adjusted to the length of the leg of the animal. The splint has holes therethrough which engage the underlying bandage to prevent the splint from slipping and which allow for ventilation of the splinted area. The splint is transparent, which allows viewing the bandage or limb without removing the splint.

16 Claims, 6 Drawing Sheets

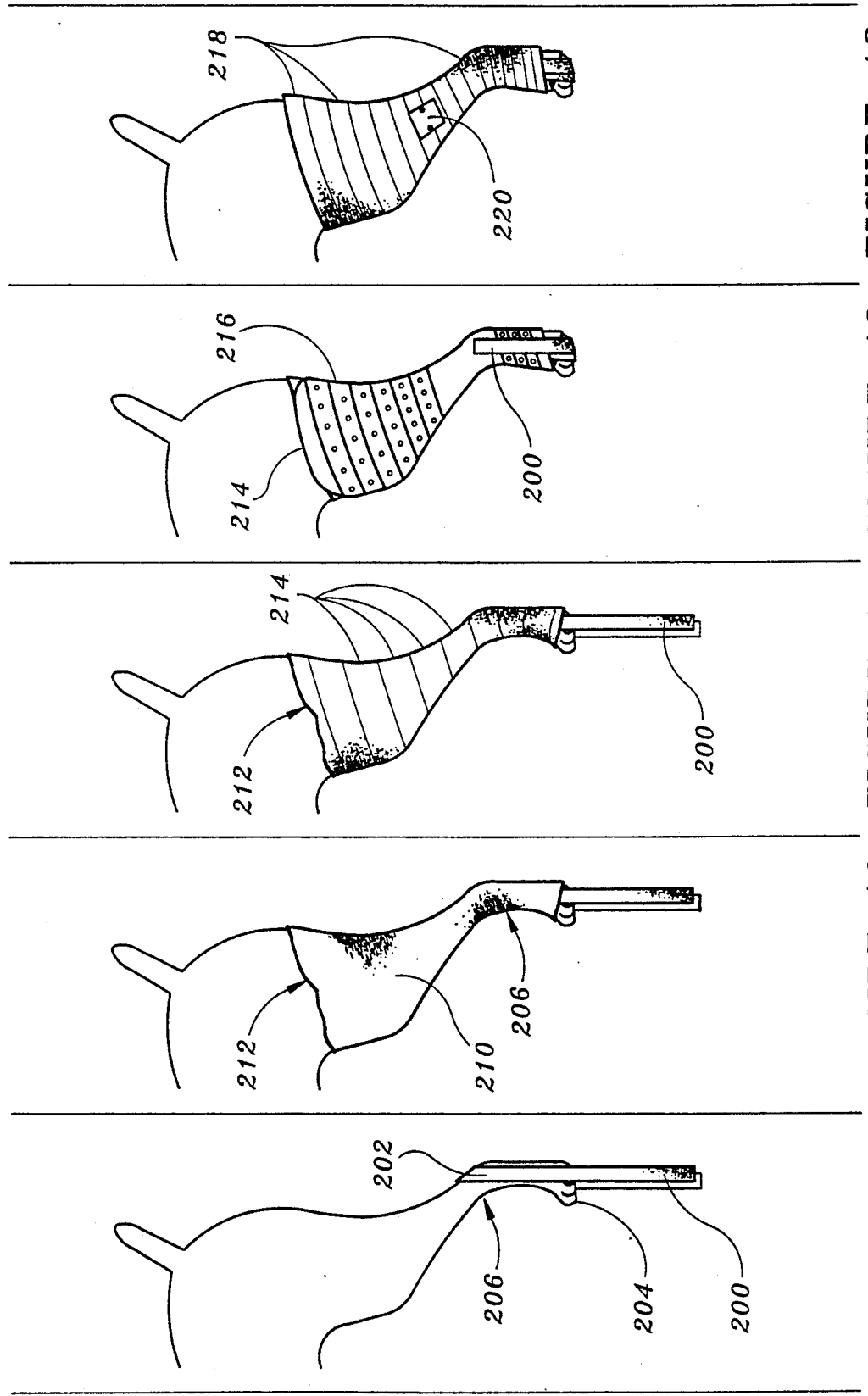

ADJUSTABLE SPLINT FOR THE LEG OF AN ANIMAL

FIELD OF THE INVENTION

The present invention relates to a device for immobilizing the legs of animals such as dogs and cats.

BACKGROUND OF THE INVENTION

It has been a long established practice to use splints or casts to immobilize the legs of animals when they are traumatized and/or broken. In order to immobilize a leg it has been necessary to construct a shaped splint or cast for each leg to be treated. The splinting or casting of a leg in this way is time consuming and both limits the ability of an underlying bandage to breath and the ability of the doctor to view either the wound or the bandage.

These difficulties have been overcome in part by the teaching of U.S. Pat. No. 3,881,472 wherein molded plastic splints, suitable for the front leg of a dog or cat, are disclosed. However, these splints all have receiving elements for the paw of the animal. While the paw receiving element does help maintain the splint in position, it requires that the splint be sized for the animal and thus a stock of multiple size splints must be maintained.

Similarly, U.S. Pat. No. 4,361,143 teaches a splint for the rear leg of an animal such as a dog or cat which has an enlarged region of the splint for receiving the paw of the animal. This splint also has a bent and enlarged region shaped to receive the stifle joint of the animal. This configuration makes the sizing of the splint even more critical.

Thus, there is a need for a molded splint that can be maintained in position without the paw receiving element. There is also the need for a molded splint which is less disruptive with regards to the ability of the underlying bandage to breathe than other splints and will permit viewing of the bandage and/or wound. In the prior art, in order to view the wound it was necessary to provide a window in the splint or cast or, alternatively, the splint could be removed to check the condition.

Thus, there is a need for a splint which is easily adaptable to animals of various sizes, provides ventilation to the region under the splint, and allows viewing the areas under the splint.

SUMMARY OF THE INVENTION

It is an object of the present invention to provide a splint for immobilizing the leg of an animal such as a dog or cat.

It is another object of the invention to provide a splint for protecting an injured leg from trauma during recovery.

It is a further object of the invention to provide a splint which will provide support to the leg when walking.

It is yet another object of the invention to provide a splint, the length of which can be adjusted to the length of the leg of the animal.

It is still a further object of the invention to provide a splint which can be used in combination with a bandage and, when so used, provides ventilation of the splinted area of the bandage.

It is a further object of the invention to provide a splint which allows for viewing the bandage or underlying leg.

It is yet another object of the invention to provide a splint which mechanically engages a bandage and prevents slippage between the splint and the bandage.

These and other objects of the present invention will become apparent from the following figures and description.

The splint of the present invention, in its simplest form, is a rigid elongated member for support of a leg of an animal. The splint has a first section which terminates in a proximal end and a second section which terminates in a distal end. The proximal end is the end closest to the point at which the leg is attached to the body, and the distal end is the end furthest from the point of attachment. The rigid elongated member has a first side and a second side. When a bandage is placed over the injured leg the first side of the rigid elongated member engages the bandage, and the second side of the rigid elongated member is engaged by a wrapping. The rigid elongated member preferably is configured such that the first side is concave and forms an elongated cavity, so as to increase the contact with the bandage around the injured leg. The cross section of the cavity will vary depending on whether a front or rear leg is to be immobilized. It is further preferred that the second side of the rigid elongated member is convex and that the two sides are spaced apart providing a wall of thickness t between about 0.075 and 0.15 inches.

The first section of the rigid elongated member has a first series of spaced apart grooves, parallel to the proximal end. Similarly, the second section of the rigid elongated member has a second series of spaced apart grooves, parallel to the distal end. The depth of the grooves in the rigid elongated member is about one half the wall thickness t. Preferably the grooves have a profile such that the bases of the grooves are substantially flat, making cutting along the grooves with heavy scissors or a utility knife easier. The length of the splint is adjusted by cutting the rigid elongated member at a selected groove to shorten the splint to the appropriate length for the length of the leg to be splinted. The splint can be shortened at the proximal end, at the distal end, or at both ends depending on the need for the particular case. When the splint is curved, it is further preferred that the grooves are in the second side of the rigid elongated member, so that positioning the grooves facilitates cutting the splint with scissors by ensuring that the blade of the scissors will not slip on the convex surface.

The splint of the present invention has holes distributed throughout the rigid elongated member. These holes pass from the first side to the second side of the rigid elongated member. Preferably the holes are distributed throughout the rigid elongated member such that they are excluded from the grooves. Having the holes in this preferred configuration will allow the length of the splint to be shortened by cutting or fracturing the rigid elongated member along the grooves without introducing irregularities along the cut edge.

It is further preferred that the holes have sloped side walls terminating at openings on the first side and the second side of the rigid elongated member. Preferably the side walls slope such that the opening on the first side of the rigid elongated member is smaller than the opening on the second side of the rigid elongated member. With such a configuration, the walls of the holes preferably form an angle $\beta_1$ of about 85 degrees with the first side of the rigid elongated member. The holes provide ventilation, and the angle $\beta_1$ of the sides of the holes helps to prevent the splint from slipping with respect to the bandage when the splint is applied over a bandage, since the holes will tend to grip the bandage. It is still further preferred that the holes in the rigid elongated member are at least $\frac{1}{8}$ of an inch in diameter at the first side.

When the rigid elongated member forms a splint suitable for use on a front leg, the cavity created by the concave surface of the first side of the rigid elongated member has a uniform cross section throughout the first section and the second section. The cross section of the cavity has an area which is bounded by a curved surface and a straight line. Preferably the curved surface approximates a circular arc. It is further preferred that the circular arc is about 130 degrees. For a front leg splint it is still further preferred that the cavities in the first section and the second section have concave surfaces which have a common axis.

The rigid elongated member forms a splint for use on the rear leg when the cavity of the first section of the rigid elongated member has a variable cross section. The cross section is bounded by a curved surface, which preferably approximates a circular arc, and a straight line where it joins the second section and widens, becoming approximate to a planar surface, close to the proximal end. The cavity of the second section has a cross section of uniform area which is bounded by a curved surface and a straight line. The second section mates with the first section. The second section preferably has a curved surface which approximates a circular arc generated about a second section axis. This axis intersects the line of traverse for the bone of the upper leg such that the included angle $\beta_2$ is about 130 degrees so as to place the leg in the normal standing position. It is further preferred that for the section of uniform cross section which terminates in the distal end, that the grooves and the distal end form an angle $\beta_3$ of about 70 degrees with the axis for the circular section.

Preferably the rigid elongated member is a transparent plastic so the bandage can be viewed through the splint. It is further preferred that there is a central section of the rigid elongated member which does not have holes. This hole free region serves as an unobstructed viewing window and protects the underlying region from dirt and other foreign matter.

BRIEF DESCRIPTION OF THE FIGURES

FIGS. 9-13 illustrates an example of a preferred method for applying the splint of the present invention to the rear leg of an animal and providing a restraining soft bandage system.

BEST MODE FOR CARRYING THE INVENTION INTO PRACTICE

Figure 1:
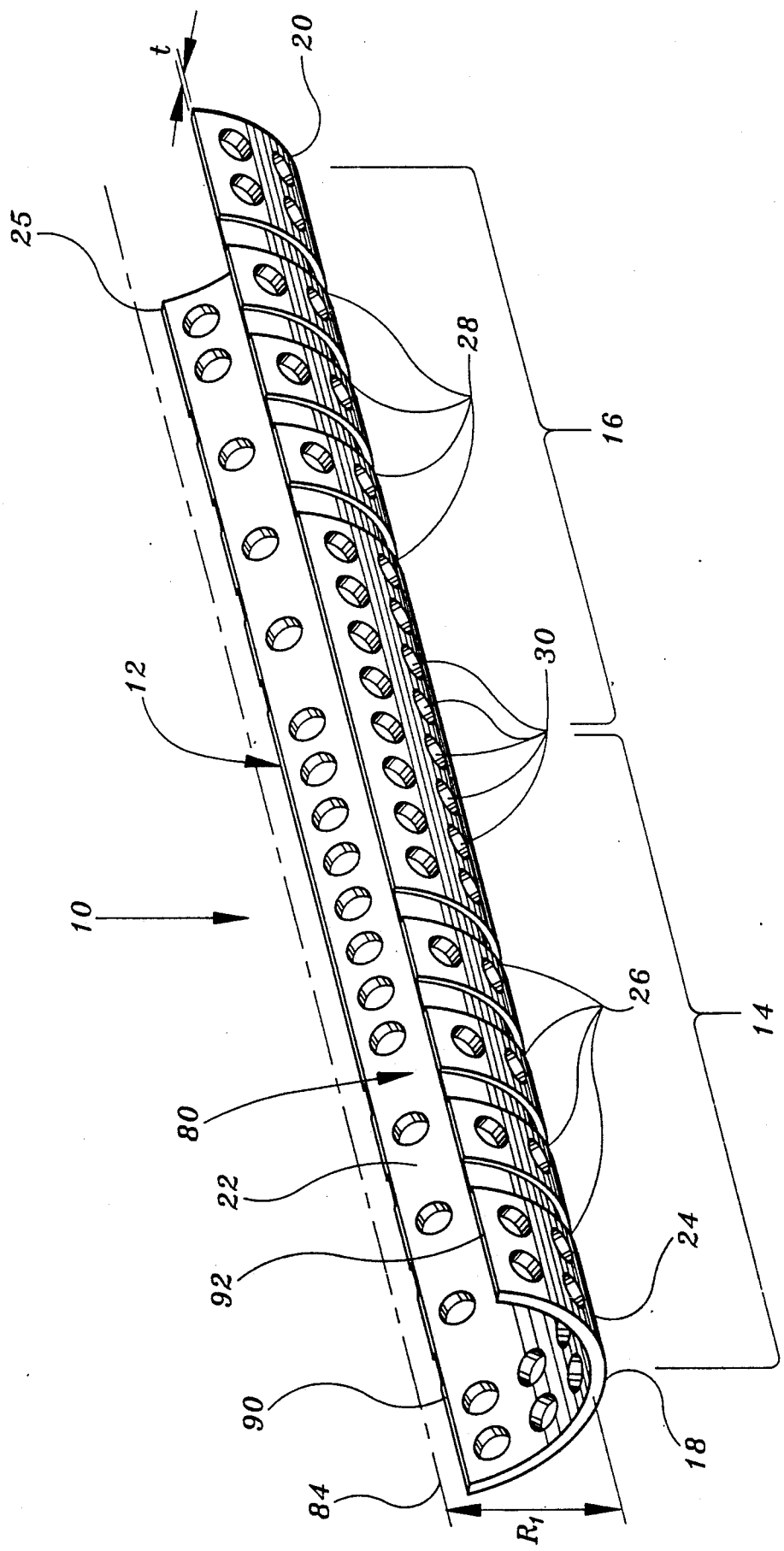
FIG. 1 is a perspective view which illustrates the shape of the front leg splint.

FIG. 1 illustrates one embodiment of the splint 10 of the present invention which is suitable for use on the front leg of an animal such as a dog or cat. The splint 10 has a rigid elongated member 12 which supports the leg of the animal. The rigid elongated member 12 has a first section 14 and a second section 16. The first section 14 terminates in a proximal end 18, while the second section 16 terminates in a distal end 20. The proximal end 18 is the end closest to the point at which the leg attaches to the body of the animal. The distal end 20 is the end which is furthest from the body of the animal. The rigid elongated member 12 has a first side 22 and a second side 24. When the splint is used in combination with a bandage, the first side 22 engages the bandage (not shown) while the second side 24 is engaged by a wrapping (not shown). The combination provides a dressing with sufficient integrity to immobilize an injured leg of an animal.

It is preferred that the rigid elongated member 12 is configured such that the first side 22 is concave. This increases the contact between the rigid elongated member 12 and the underlying bandage. It is further preferred that the second side 24 of the rigid elongated member 12 is convex and that the two sides are spaced apart providing a wall 25 having a thickness t of between about 0.075 inches and 0.15 inches.

The first section 14 of the rigid elongated member 12 has a first series of spaced apart grooves 26 which are parallel to the proximal end 18. Similarly, the second section 16 of the rigid elongated member 12 has a second series of spaced apart grooves 28. The first series of grooves 26 and the second series of grooves 28 provide a means for adjusting the length of the rigid elongated member 12. Each groove in the first series of grooves 26 and the second series of grooves 28 provides a path for cutting the rigid elongated member 12.

Holes 30 are distributed throughout the rigid elongated member 12. The holes 30 pass from the first side 22 of the rigid elongated member 12 to the second side 24 of the rigid elongated member 12, providing ventilation and drainage for the underlying bandage. It is further preferred that the holes 30 are distributed such that the holes 30 are excluded from the first series of grooves 26 and the second series of grooves 28. Having the holes 30 excluded from the grooves in the series of grooves 26 and the series of grooves 28 eliminates irregularities resulting from holes along the end of the rigid elongated member 12 after adjusting the length by cutting the rigid elongated member 12 along the grooves.

Figure 2:
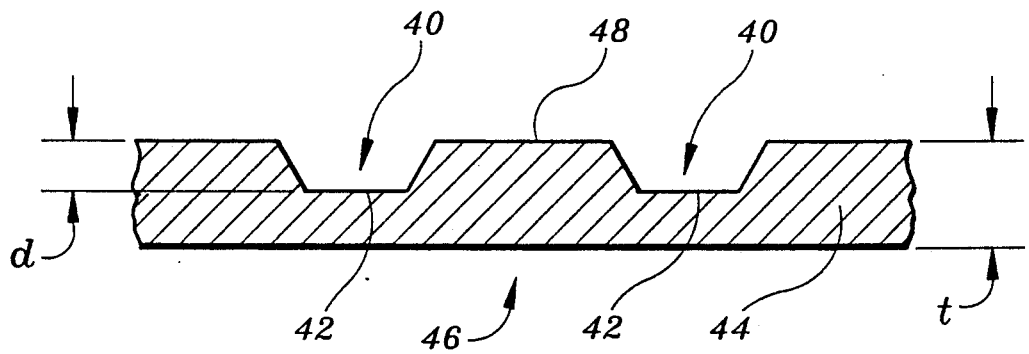
FIG. 2 illustrates a preferred groove profile for a splint of the present invention.

A preferred profile for the grooves 40 is illustrated in FIG. 2. The grooves 40 are contoured such that the bases 42 of the grooves 40 are substantially flat. This provides a flat surface to cut either with a utility knife or a pair of scissors. It is further preferred that the depth $d_1$ of the grooves 40 be about $\frac{1}{2}$ of the thickness t of the wall 44 of the rigid elongated member 46. When the splint is curved it is further preferred that the grooves 40 be in the second side 48 which is the convex side of the rigid elongated member 46.

Figure 3:
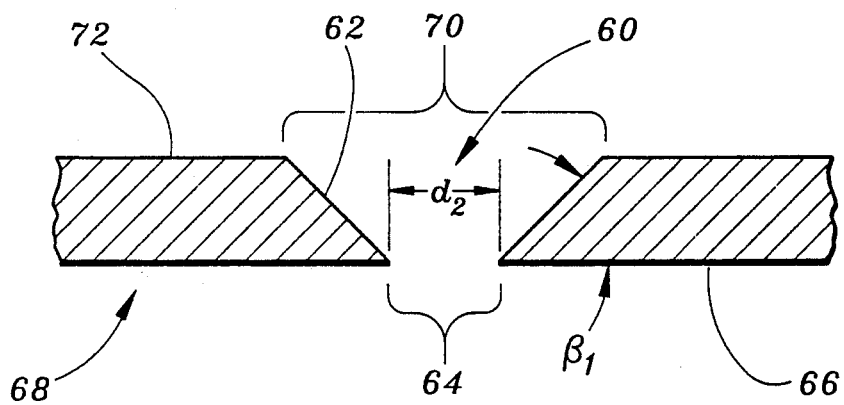
FIG. 3 illustrates a preferred sidewall orientation for a splint of the present invention.

Preferably the walls of the holes 60 are sloped, as shown in FIG. 3. The holes 60 have a sloped sidewall 62 having a first opening 64 on the first side 66 of the rigid elongated member 68 which is smaller than the second opening 70 on the second side 72 of the rigid elongated member 68. When circular holes are employed it is preferred that the holes 60 have a minimum diameter $d_2$ of at least ⅜ of an inch. This minimal dimension is on the first side 66 which is the side of the rigid elongated member 68 which will engage an underlying bandage when such is employed. With this configuration the bandage will be engaged by the holes 60. The sidewall 62 forms an acute angle $\beta_1$ with respect to the first side 66 of the rigid elongated member 68. This acute angle $\beta_1$ provides an edge which further assists in preventing slippage between a bandage and the rigid elongated member 68. The acute angle $\beta_1$ is preferably about 85 degrees.

For the front leg splint, as shown in FIG. 1, the concave surface formed by the first side 22 provides a cavity 80 having a uniform cross section 82 in the first section 14 and the second section 16 of the rigid elongated member 12. The cavity 80 in the first section 14 and the cavity 80 in the second section 16 have a common axis 84.

Figure 4:
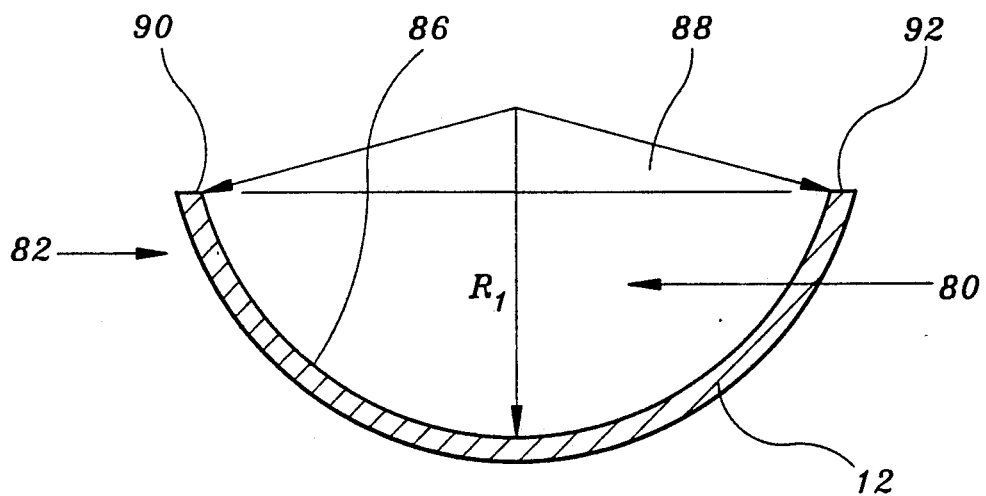
FIG. 4 is an end view of the splint of FIG. 1 which illustrates a preferred cross section of a front leg splint.

FIG. 4 is an end view of FIG. 1 showing the cavity 80 in cross section and illustrating the area of the cross section. The cross section of the cavity 80 has a cross section area 82 which is bounded by a curved surface, which for the preferred illustration approximates a circular arc 86 of radius $R_1$, and a straight line, which is a cord 88 of the circular arc 86 of radius $R_1$. The cord 88 intersects at first edge 90 of the rigid elongated member 12 and the second edge 92 of the rigid elongated member 12. Preferably the arc of a le 86 is about 130 degrees. Having the cavity 80 so defined provides sufficient stability for the leg while providing options for placement of the splint in different locations.

Figure 5:
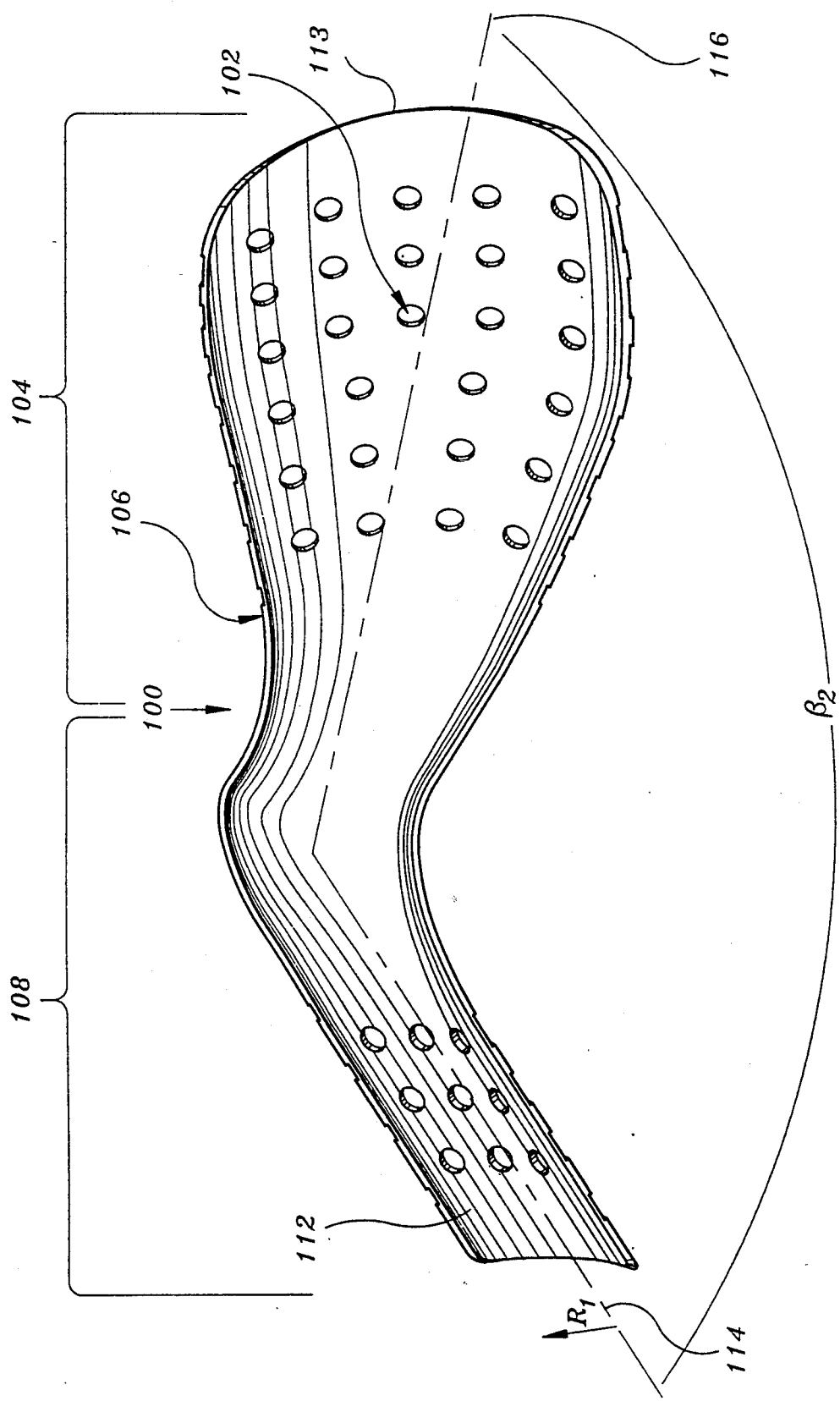
FIG. 5 is a perspective view which illustrates the shape of the rear leg splint.

FIG. 5 illustrates a splint suitable for immobilizing the hind leg of a cat or dog. FIG. 5 shows a rear leg splint which may be used on the outside of the left leg as a left lateral splint or on the inside of the right leg as a right medial splint. The splint 100 has a central cavity 102 which is not of uniform cross section. The first section 104 of the central cavity 102 of the rigid elongated member 106 is of variable cross section. The second section 108 of the central cavity 102 is of uniform cross section and the cavity of the second section 108 has curved surface 112, which approximates a circular arc. The first section 104 is contoured to match the contour of the second section 108 where they meet and widens as it approaches the proximal end 113 where the surface of the cavity 102 flattens and becomes approximately planar.

Preferably the second section 108 of the central cavity 102 has a cross section bounded by a curved surface which, for the preferred embodiment of FIG. 5, approximates a circular arc of radius $R_2$ and a straight line. The second section 108 has a second section axis 114. This second section axis 114 is so positioned that it intersects the line of traverse 116 of the bone of the upper leg, providing an included angle $\beta_2$ of about 130 degrees. Maintaining the included angle $\beta_2$ at about 130 degrees allows the leg to be maintained in its normal standing position.

Figure 6:
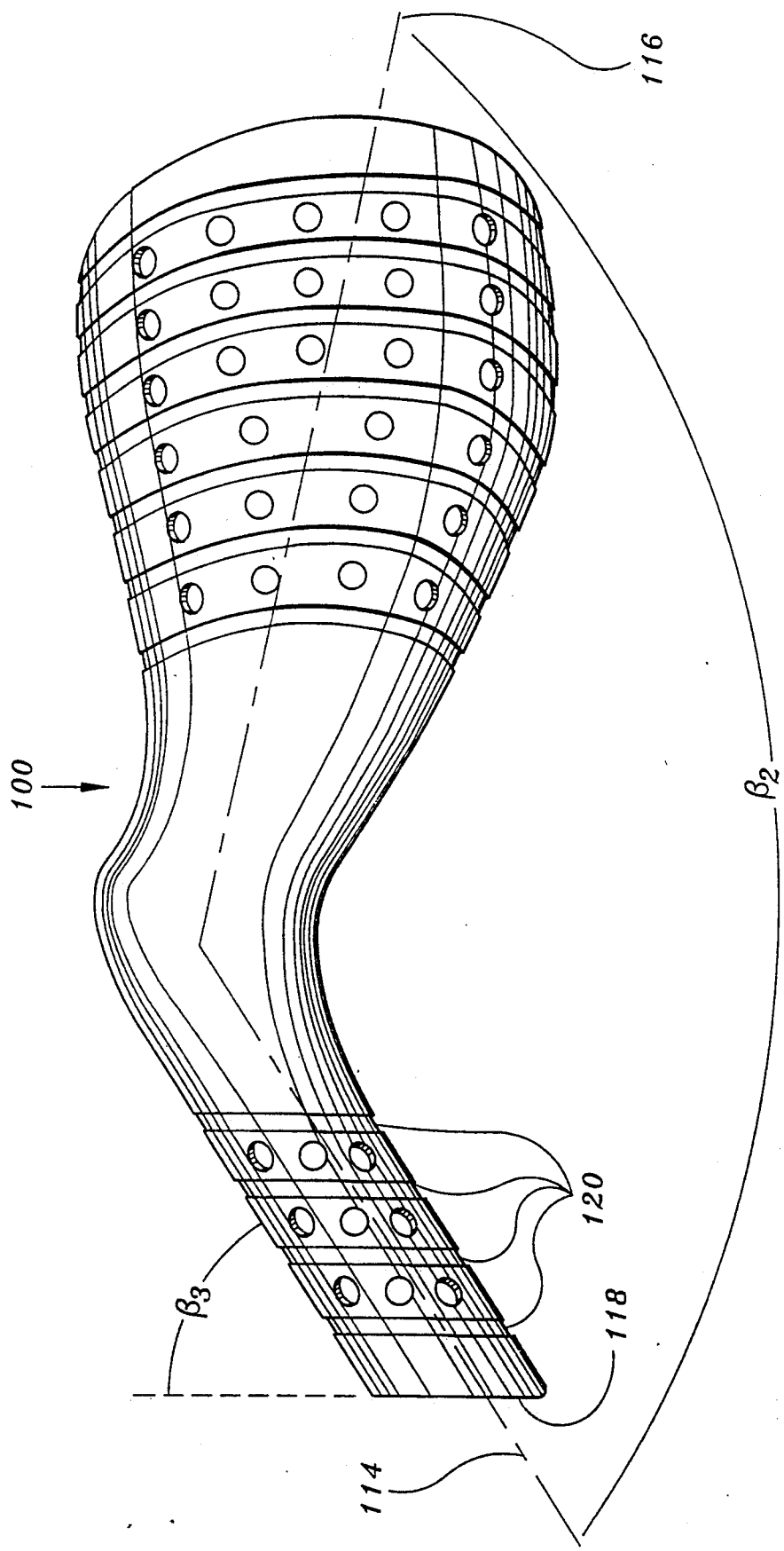
FIG. 6 illustrates a side view of a rear leg splint which is the mirror image of the splint shown in FIG. 4.

FIG. 6 illustrates a splint which is the mirror image of the splint of FIG. 5. This splint is suitable for use on the inside of the left leg as a left medial splint or on the outside of the right leg as a right lateral splint. The splint illustrates the preferred distal end 118 configuration. The splint 100 is configured such that the second section axis 114 will intersect the line of traverse of the bone of the upper leg at an angle $\beta_2$ of about 130. When $\beta_2$ is about 130 degrees the distal end 118 should preferably make an angle $\beta_3$ with respect to the second section axis 114 of about 70 degrees. The angle $\beta_3$ is the included angle between the front edge of the splint and the distal end 118. Having the splint distal end 118 so configured ensures that the animal can place its paw in the normal standing position.

Figure 7:
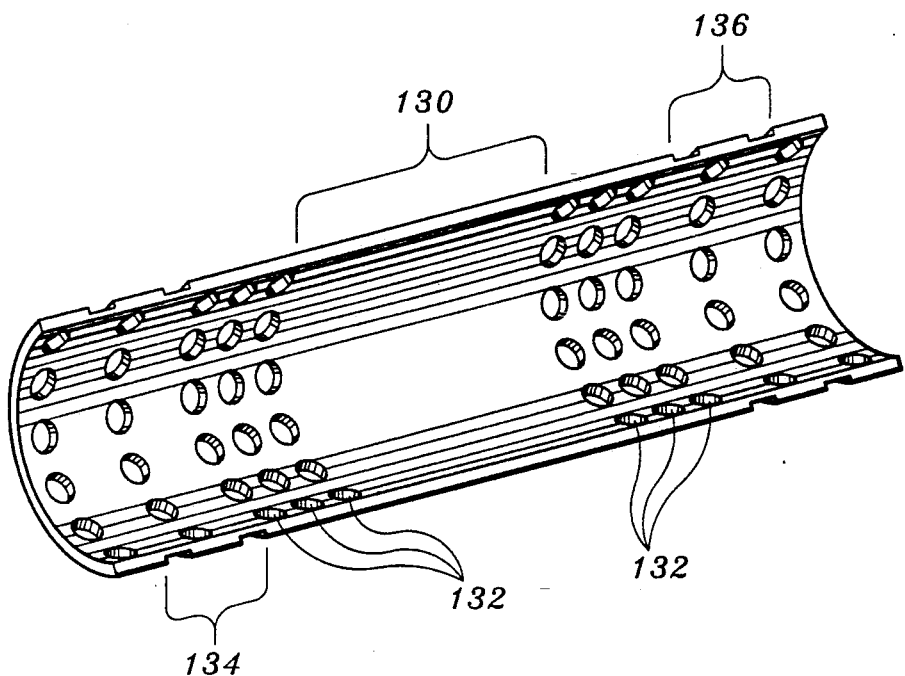
FIG. 7 illustrates a preferred embodiment of a front leg splint with a hole free central region.

FIG. 7 illustrates a preferred embodiment of the front leg splint in which there is a center region 130 which is free from holes 132. Preferably the center region 130, which is located between the first series of spaced apart grooves 134 and the second series of spaced apart grooves 136, is made of solid transparent plastic. The center region 130 can serve as a window to allow viewing of the underlying bandage or wound and keep dirt and other foreign matter out.

Figure 8:
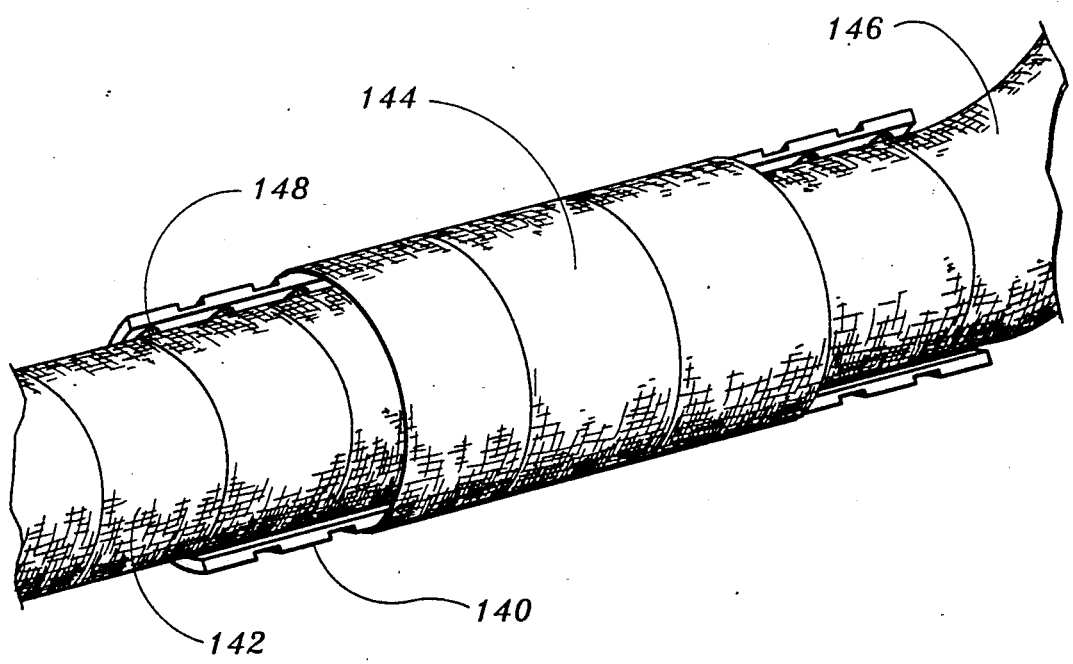
FIG. 8 illustrates a soft bandage system applied to the front leg of an animal employing one embodiment of the splint of the present invention.

FIG. 8 illustrates a soft bandage system employing the splint 140 of the present invention. As illustrated a splint 140, such as shown in FIG. 1, is used in combination with a soft bandage 142 and with an outer wrapping 144. The traumatized leg 146 of the animal is wrapped with soft bandages 142 to provide a padded region to protect any lesions or bony protrusions. The splint 140 is positioned over the soft bandages 142. The soft bandage 142 ensures that the splint will provide distributed support, since the soft bandage 142 will fill in depressions. Preferably the soft bandage 142 will engage the holes 148, and the angled side walls, as illustrated in FIG. 3, will grip the soft bandage 142 which engages the holes 148 to prevent slippage. An outer wrapping 144, such as an elastic bandage or tape, is applied over the splint 140 to secure the splint 140 and soft bandage 142 relative to the leg 146. In the case of bandaging the front leg, since the cross section is uniform the pressure from the outer wrap is sufficient to maintain the bandage.

When the splint of the present invention is used on the rear leg of an animal as part of a soft bandage system, it is preferred, because of the tapered cross section of the leg, to employ a stirrup to secure the soft bandage system. A preferred method of applying a bandage system is illustrated in FIGS. 9–13.

FIG. 9 shows adhesive tape 200 applied to both the lateral side 202 and the medial side 204 of the tarsus 206. The tape 200 extends beyond the foot of the animal. The tape 200 forms a stirrup which is used to secure the bandage.

FIG. 10 shows a soft pad bandage 210, such as roll cotton or cast padding which is applied over the leg 212 and tarsus to provide a cushion and fill in depressions in the shape of the leg and protect any lesions and bony protuberances.

FIG. 11 shows the soft pad 212 wrapped with a strip gauze 214, such as roll gauze or stretch gauze, which is used to cover the padding and produce a dressing with a smooth curved surface that will fit snugly into a splint.

FIG. 12 shows a splint 216, similar to the splint shown in FIGS. 5 and 6, placed on the dressing applied to the leg. The splint has been shortened to the appropriate length at both the proximal and distal ends by cutting along the grooves. The adhesive tape stirrup is folded back on the splint and strip gauze 214.

FIG. 13 shows an outer wrapping of porous adhesive tape or elastic tape. The tape is applied over the splint going from the distal to the proximal end. Any desired window areas 220 may be left free of tape.

While the novel features of the present apparatus have been described in terms of particular embodiments and preferred applications, it should be appreciated by one skilled in the art that substitutions of materials and details obviously can be made without departing from the spirit of the invention.

I claim:

1. An improved splint for immobilizing a leg of an animal, the splint forming a rigid elongated member having a first side and a second side with the first side being concave, providing an elongated cavity, the improvement comprising:

holes passing through the rigid elongated member from the first side to the second side, said holes having sloped side walls such that an acute angle $\beta_1$ is formed between a side wall and the first side of the rigid elongated member.

2. The splint of claim 1 wherein said holes are circular and have a minimum diameter $d_2$ of at least about ⅛ of an inch.

3. The splint of claim 1 wherein the rigid elongated member is a transparent plastic material.

4. The improved splint of claim 1 wherein the rigid elongated member is a transparent plastic member and further wherein each groove of said first series of grooves and said second series of grooves has a profile such that the base of each groove forms a substantially flat surface and said first series of grooves and said second series of grooves reside in the second side of the rigid elongated member.

5. The improved splint of claim 4 wherein the rigid elongated member has a central section which is hole free, thereby providing a window for viewing while preventing dirt and other matter access to the area beneath.

6. The improved splint of claim 1 for use on a front leg, wherein the rigid elongated member is a transparent plastic member and further the elongated cavity has a first cavity section and a second cavity section having a uniform cross section.

7. The improved splint of claim 6 wherein said uniform cross section is bounded by a line and a curved surface, said curved surface being a circular arc.

8. The improved splint of claim 7 wherein said circular arc is about 130 degrees.

9. The improved splint of claim 1 for use on the rear leg of an animal wherein the rigid elongated member is a transparent plastic member and further wherein said elongated cavity has a cross section in said first section of the rigid elongated member which is variable, being curved and approximating a circular arc as it approaches said second section of the rigid elongated member and approximately a planar surface as it approaches said proximal end to accommodate the bone of the upper leg and furthermore wherein said second section has a uniform cross section having a second section axis.

10. The improved splint of claim 9 wherein said second section axis intersects the line of traverse of the bone of the upper leg such that the included angle $\beta_2$ is about 130 degrees.

11. The improved splint of claim 10 wherein said second section axis intersects said distal end and said series of spaced apart grooves at an angle $\beta_{23}$ of about 70 degrees.

12. The improved splint of claim 11 wherein said first series of spaced apart grooves and said second series of spaced apart grooves are so positioned to provide a groove free region therebetween, and further wherein said holes are randomly spaced in said groove free region of said rigid elongated member.

13. The improved splint of claim 6 wherein said first series of spaced apart grooves and said second series of spaced apart grooves are so positioned to provide a groove free region therebetween, and further wherein said holes are randomly spaced in said groove free region of said rigid elongated member.

14. A soft bandage system for a rear leg of an animal comprising:

said improved splint of claim 12;

a stirrup for application to the leg of the animal;

a dressing for application to the leg over said dressing engaging said holes in said rigid elongated member of said splint; and an outer wrap to be applied over said splint and siad dressing.

15. A soft bandage system for the front leg of an animal comprising:

said improved splint of claim 13;

a stirrup for application to the leg of an animal;

a dressing for application to the leg, said dressing engaging said holes in said rigid elongated member of said splint; and an outer wrap to be applied over said splint and said dressing.

16. The improved splint of claim 1 further comprising:

a first series of spaced apart grooves which are incorporated in said first section and which are substantially parallel to said proximal end; and a second series of spaced apart grooves which are incorporated in said second section and which are substantially parallel to said distal end terminate at said first edge and said second edge;

and further wherein said holes are distributed such that they are excluded from said first series of spaced apart grooves and said second series of spaced apart grooves and said acute angle $\beta_2$ is about 85 degrees.

* * * * *